(12) United States Patent
Little et al.

(10) Patent No.: US 9,295,581 B2
(45) Date of Patent: Mar. 29, 2016

(54) MEDICAL TACK WITH A VARIABLE EFFECTIVE LENGTH

(75) Inventors: James S. Little, Saugus, CA (US);
Gaillard R. Nolan, Valencia, CA (US);
Neil H. Talbot, Montrose, CA (US);
Robert J. Greenberg, Los Angeles, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 1385 days.

(21) Appl. No.: 11/352,168

(22) Filed: Feb. 13, 2006

(65) Prior Publication Data
US 2006/0155288 A1  Jul. 13, 2006

Related U.S. Application Data

(63) Continuation of application No. 09/975,427, filed on Oct. 10, 2001, now abandoned.

(51) Int. Cl.
| | |
|---|---|
| *A61F 2/16* | (2006.01) |
| *A61F 9/007* | (2006.01) |
| *A61B 17/064* | (2006.01) |
| *A61B 17/068* | (2006.01) |
| *A61F 11/00* | (2006.01) |
| *A61B 17/10* | (2006.01) |

(52) U.S. Cl.
CPC ........... *A61F 9/00727* (2013.01); *A61B 17/064* (2013.01); *A61B 17/068* (2013.01); *A61F 11/004* (2013.01); *A61B 17/10* (2013.01); *A61B 2017/0646* (2013.01); *A61B 2017/0647* (2013.01)

(58) Field of Classification Search
CPC .................... A61B 2017/0647; A61F 9/00727
USPC ......... 623/6.12; 606/184, 107, 108, 166, 167, 606/185, 170, 75, 329; 24/106, 107, 24/706.1–711.5
See application file for complete search history.

(56) References Cited

U.S. PATENT DOCUMENTS

| | | | | | |
|---|---|---|---|---|---|
| 1,857,158 | A | * | 5/1932 | Maloney | 248/685 |
| 1,911,490 | A | * | 5/1933 | Carter | 267/48 |
| 2,062,760 | A | * | 12/1936 | Overstrom | 267/165 |
| 3,434,095 | A | * | 3/1969 | DeRose | 439/47 |
| 3,769,774 | A | * | 11/1973 | Barnes | 52/698 |
| 3,842,709 | A | * | 10/1974 | Fuqua | 411/350 |
| 3,892,013 | A | * | 7/1975 | Gould | 24/114.4 |
| 3,896,599 | A | * | 7/1975 | Werstein et al. | 52/704 |
| 3,934,315 | A | * | 1/1976 | Millheiser et al. | 24/453 |
| 4,005,507 | A | * | 2/1977 | Yamazaki | 24/351 |
| 4,106,745 | A | * | 8/1978 | Carrow | 249/97 |
| 4,369,530 | A | * | 1/1983 | Robinson et al. | 623/3.24 |
| 4,427,328 | A | * | 1/1984 | Kojima | 411/508 |
| 4,439,198 | A | * | 3/1984 | Brightman et al. | 424/426 |
| 4,532,926 | A | * | 8/1985 | O'Holla | 606/220 |
| 4,712,550 | A | * | 12/1987 | Sinnett | 606/151 |
| 4,747,739 | A | * | 5/1988 | Bowman et al. | 411/368 |
| 4,886,405 | A | * | 12/1989 | Blomberg | 411/16 |
| 4,924,865 | A | * | 5/1990 | Bays et al. | 606/77 |
| 5,031,756 | A | * | 7/1991 | Buzzard et al. | 206/308.2 |

(Continued)

*Primary Examiner* — Katherine M Shi
(74) *Attorney, Agent, or Firm* — Scott B. Dunbar

(57) ABSTRACT

The present invention is an improved medical tack. The tack of the present invention includes attachment points at each end where at least one of the attachment points is moveable, varying the effective length of the tack. Varying the length of the medical tack adapts the tack for use with tissue of different thickness.

21 Claims, 8 Drawing Sheets

(56) References Cited

U.S. PATENT DOCUMENTS

| | | | |
|---|---|---|---|
| 5,109,844 A | 5/1992 | de Juan, Jr. et al. | |
| 5,231,993 A * | 8/1993 | Haber et al. | 600/583 |
| 5,316,422 A * | 5/1994 | Coffman | 411/107 |
| 5,346,459 A * | 9/1994 | Allen | 606/185 |
| 5,368,261 A * | 11/1994 | Caveney et al. | 248/73 |
| 5,431,634 A * | 7/1995 | Brown | 604/153 |
| 5,935,155 A | 8/1999 | Humayun et al. | |
| 6,165,192 A | 12/2000 | Greenberg et al. | |
| 6,276,030 B1 * | 8/2001 | Smith | 24/115 G |
| 6,309,158 B1 * | 10/2001 | Bellinghausen et al. | 411/353 |
| 6,312,434 B1 * | 11/2001 | Sutrina et al. | 606/127 |
| 6,338,649 B1 * | 1/2002 | Smith | 439/504 |
| 6,644,903 B1 * | 11/2003 | Arand | 411/352 |
| 6,719,750 B2 * | 4/2004 | Varner et al. | 604/289 |
| 6,863,677 B2 * | 3/2005 | Breznock | 606/184 |

* cited by examiner

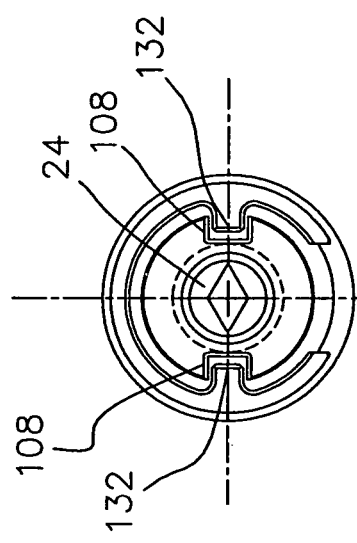
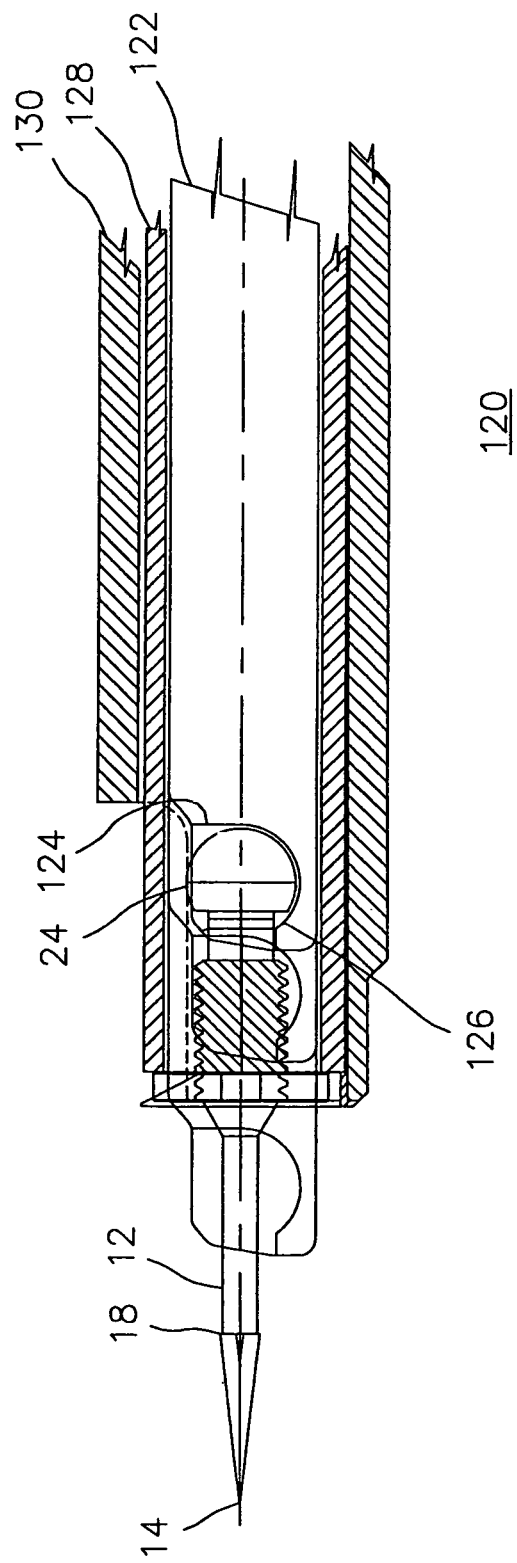
FIG. 8
FIG. 7

MEDICAL TACK WITH A VARIABLE EFFECTIVE LENGTH

CROSS REFERENCE TO RELATED APPLICATIONS

This application is a continuation of U.S. applications Ser. No. 09/975,427, filed Oct. 10, 2001, now abandoned, entitled Medical Tack With A Variable Effective Length. This application is related to U.S. patent application Ser. No. 09/225,267, filed Jun. 5, 1999, now U.S. Pat. No. 6,165,192, for Method and Apparatus for Intraocular Retinal Tack Inserter and U.S. patent application Ser. No. 09/783,236, now U.S. Pat. No. 7,338,522, for Implantable Retinal Electrode Array Configuration for Minimal Retinal Damage and Method of Reducing Retinal Stress, the disclosures of which are incorporated herein by reference.

This invention was made with government support under grant No. R24EY12893-01, awarded by the National Institutes of Health. The government has certain rights in the invention.

FIELD OF THE INVENTION

The present application relates to medical tacks, and more specifically to medical tacks designed to attach to body tissues of variable thickness.

BACKGROUND OF THE INVENTION

It has been know since the 1700s that nerves carry their signals throughout the body by electricity. Far more recently, we have learned that we can partially control those signals by applying an electrical signal to a nerve ending. One of the most difficult forms of nerve stimulation is the creation of artificial sight by electrically stimulating the retina.

U.S. Pat. No. 5,109,844 ("De Juan") and U.S. Pat. No. 5,935,155 ("Humuyan") disclose systems for the electrical stimulation of the retina by a retinal electrode array held against the retina. Retinal Tacks, first used to repair detached retinas, provide one method of attaching a retinal electrode array such as those described in De Juan and Humuyan. U.S. Pat. No. 6,165,192 ("Greenberg") describes retinal tacks and methods of implanting retinal tacks to secure a retinal electrode array.

Some prior retinal tacks pierce the retina and sclera, and attach via an integral barb to the back side of the sclera. The problem with the prior art, is that scleras vary in thickness. If a tack is too long for a given sclera, the retinal electrode array will not be held in contact with the retina, causing poor electrical contact with the retina. If the tack is too short, the retinal electrode array will apply too much force on the retina, limiting blood flow under the retinal electrode array. This limited blood flow causes a condition similar to glaucoma. The effects of glaucoma begin when the vitreous humor reaches a pressure of 0.2 g/mm$^2$. Therefore the pressure exerted by the retinal electrode array must be less than 0.2 g/mm$^2$.

Medical tacks have been used in other applications, such as reattaching a detached retina and repairing a torn eardrum. Again, the tissue behind the eardrum can vary in thickness, causing too much or too little force on the damaged eardrum when a tack is inserted. A system is needed which is capable of holding a medical device in contact with tissue, or holding two pieces of tissue together, without exerting such force on that tissue, that the tissue is damaged.

SUMMARY OF THE INVENTION

The present invention addresses these and other short comings in the prior art by providing an improved medical tack. The tack of the present invention includes attachment points at each end where at least one of the attachment points is moveable, varying the effective length of the tack. A preferred embodiment includes a barb near its point to attach to the back side of the selected tissue and an adjustable base, preferably a spring loaded adjustable base. The tack exerts controlled force on a medical device, or directly to tissue, provided that the tissue thickness is within a selected range.

BRIEF DESCRIPTION OF THE DRAWINGS

Preferred embodiments demonstrating the various objectives and features of the invention will now be described in conjunction with the following drawings:

FIG. 7 is a cross section view of an insertion tool holding a tack, showing how the tool contacts an adjustment nut.

FIG. 8 is a cross section view of the insertion and adjustment tool holding a tack at 90° to FIG. 7.

DETAILED DESCRIPTION OF THE PREFERRED EMBODIMENTS

Figure 1:
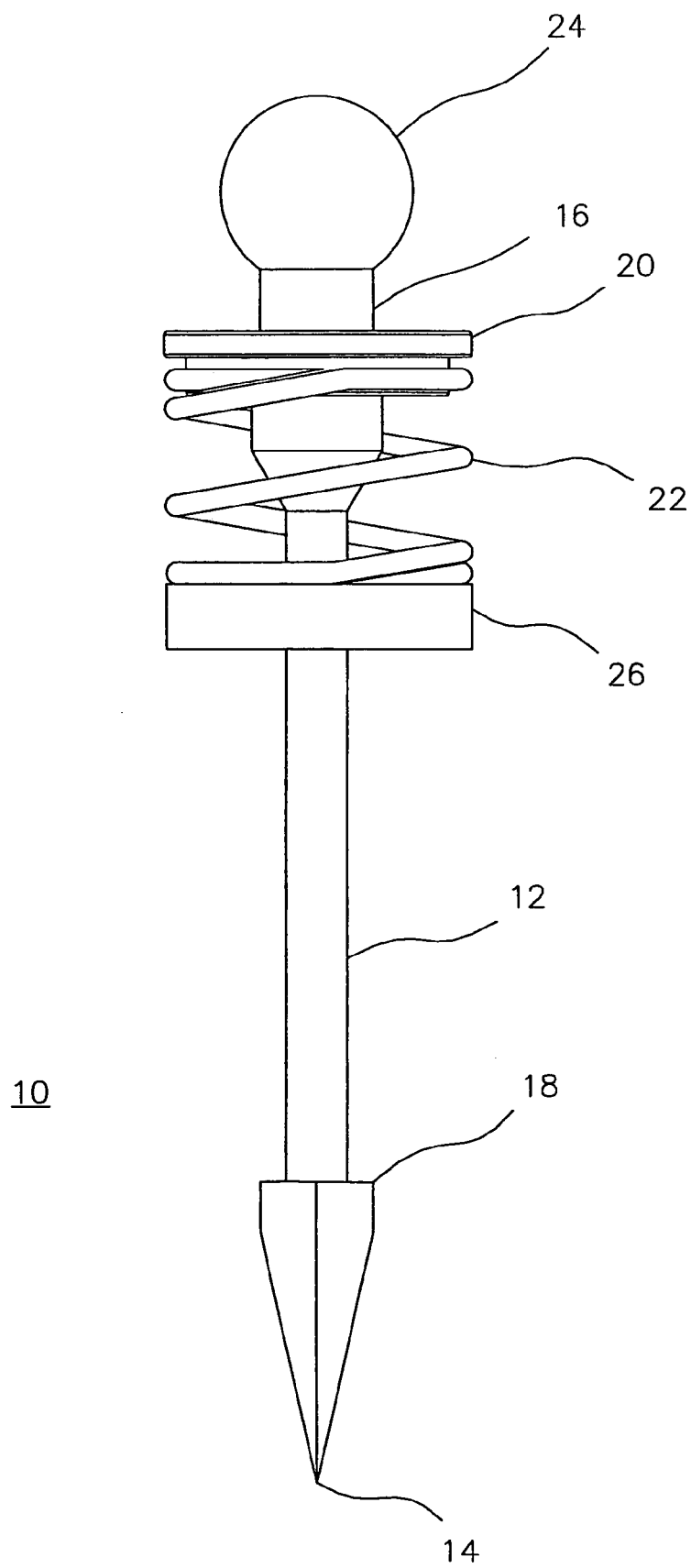
FIG. 1 the preferred retinal tack.

FIG. 1 shows the preferred retinal tack 10. The tack 10 includes a shaft 12 having a point 14 and a base 16. Just behind the point 14 is a barb 18 which hooks on the backside of the selected tissue, a sclera in the preferred embodiment, and tends to prevent the tack 10 from being withdrawn. A flange 20 is formed around the base 16 of the tack 10 to form a seat for a coil spring 22 surrounding the shaft 12. A mounting stud 24 extends beyond the flange 20 to provide an access point for an insertion tool (described later with reference to FIGS. 7 and 8).

A washer 26 is provided on the end of the spring 22, to provide even contact with a retinal electrode array 28. All of the parts of the tack 10 must be biocompatible. In the preferred embodiment, the point 14, barb 18, shaft 12, base 16, flange 20 and mounting stud 24 are all machined from a single piece of Ti-6A14V Eli (Extra Low Interstitial) Titanium. Stainless steel would also work well for fabricating the tack 10. The spring 22 is also formed from the same titanium alloy. The tack 10 and spring 22 are joined by silicone based glue (not shown). Alternatively, the washer can be placed loosely against the spring and held in place by the spring's force. The washer 26 is preferably silicone and attached to the spring by silicone based glue. Fabricating the washer 26 of silicone gives additional elastic effect. Alternatively, the washer 26 can be made of a fluoropolymer such as tetrafluorethylene (Teflon). A tetrafluorethylene washer has no elastic effect but slides more freely along the shaft 12, and thereby helps avoid stress concentrations. The electrode array 28 (as described in greater detail below with reference to FIG. 3) is made of a highly compliant material such a silicone. This is necessary to minimize damage to the retina. The washer 26 helps to spread the force of the spring 22 across a larger area of the electrode array 28, and, thereby prevent damage to the electrode array 28.

Figure 2:
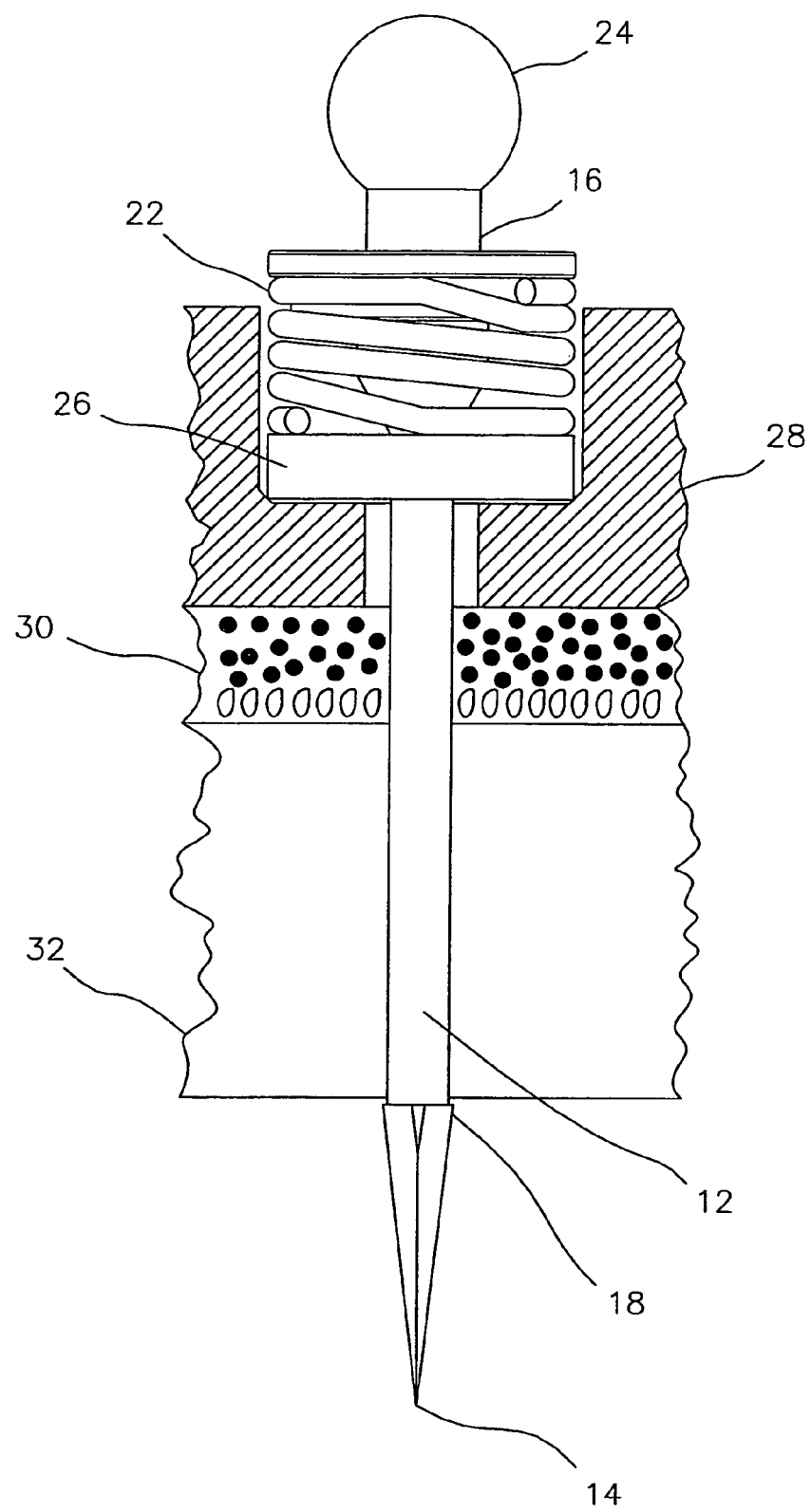
FIG. 2 the preferred retinal tack show at 90° to FIG. 1 and inserted into a retina.

As shown in FIG. 2, the tack 10 is inserted through a retina 30 and sclera 32, until the barb 18 hooks on the back side of the sclera 32. FIG. 2 shows the tack 10 viewed 90° from the view of FIG. 1. The point 14 and barb 18 form a flat blade, wider in the orientation shown in FIG. 1, than shown here in FIG. 2. The preferred spring 22 exerts a force of three grams when half loaded, and four grams when mostly compressed. Three grams of force on a 24 mm$^2$ electrode array creates a pressure of 0.124 g/mm$^2$ which is less than the 0.2 g/mm$^2$ allowable, but still sufficient to create a good contact. Four grams of force, when the spring is mostly compressed, over the 24 mm$^2$ electrode array creates a pressure of 0.167 g/mm$^2$ which is still less than the 0.2 g/mm$^2$ allowable. It should be noted that the electrode array 28 is not a rigid structure and, therefore, does not distribute the springs force evenly across the retina. While pressure on the retina may exceed 0.2 g/mm$^2$ locally around the tack 10, the area around the tack 10 is less important as explained in greater detail with respect to FIG. 3. Coil springs are well suited to the present invention, because they are highly compliant, and exhibit less force variation, over their working range, than other spring types. Coil springs are well adapted to exerting very low forces.

Retinal tacks must be made in very small dimensions. The average sclera and retina thickness is 0.04 inches with a maximum rarely exceeding 0.058 inches. This means the distance between the barb 18 and the base of the retinal electrode array 28 must be 0.058 inches when the spring is mostly relaxed and 0.040 when the spring is half compressed, to a fit the maximum number of scleras. The shaft 12 must also be small to limit trauma to the retina. The preferred tack 10 has a shaft 12 diameter of 0.007 inches.

Figure 3:
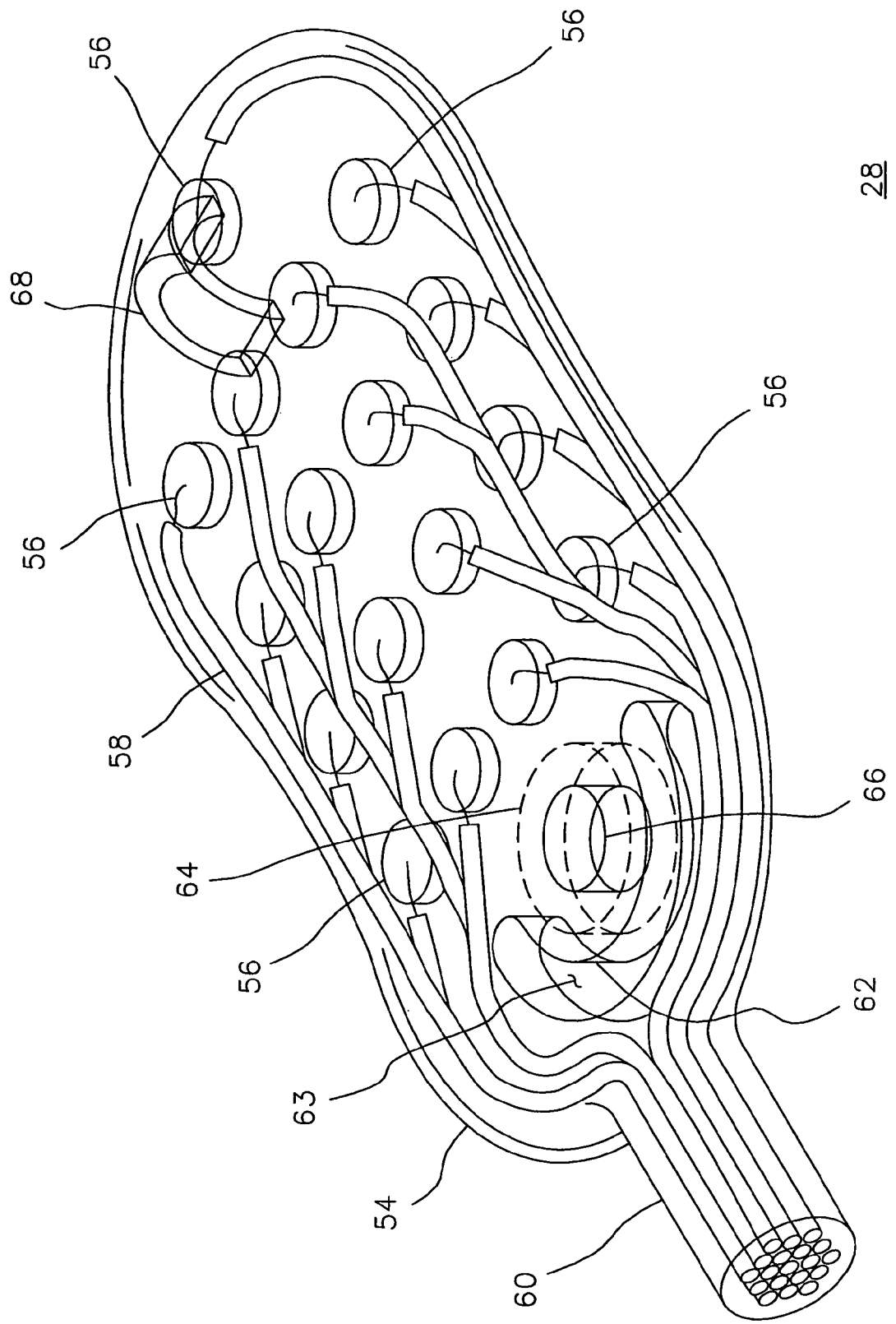
FIG. 3 is a retinal electrode array which can be secured by the preferred retinal tack.

FIG. 3 provides a isometric view of a preferred embodiment of the retinal electrode array 28, including an oval-shaped electrode array body 54, a plurality of electrodes 56 made of an electrically conductive material, such as platinum or one of its alloys, but that can be made of any conductive biocompatible material such as iridium, iridium oxide or titanium nitride. The electrodes are individually attached to separate conductors 58 made of a conductive material, such as platinum or one of its alloys, but which could be made of any biocompatible conductive material, that is enveloped within an insulating sheath 60, that is preferably silicone, that carries an electrical signal to each of the electrodes 56. "Oval-shaped" electrode array body means that the body may approximate either a square or a rectangle shape, but where the corners are rounded.

The electrode array body 54 is made of a soft material that is compatible with the body. In a preferred embodiment, the array body 54 is made of silicone having a hardness of about 50 durometer or less on the Shore A scale. It is a substantial goal to have the electrode array body 54 in intimate contact with the retina of the eye.

A strain relief internal tab 62, defined by a strain relief slot 63 that passes through the array body 54, contains a mounting aperture 66 for fixation of the electrode array body 54 to the retina of the eye by use of the tack 10. A reinforcing ring 64 is colored and opaque to facilitate locating the mounting aperture 66 during surgery and may be made of tougher material, such as higher hardness silicone, than the body of the electrode array body 54 to guard against tearing.

A grasping handle 68 is located on the surface of the electrode array body 54 to enable its placement by a surgeon using forceps or by placing a surgical tool into the hole formed by the grasping handle 68. The grasping handle 68 avoids damage to the electrode body that might be caused by the surgeon grasping the electrode body directly. The grasping handle 68 also minimizes trauma and stress-related damage to the eye during surgical implantation by providing the surgeon a convenient method of manipulating the electrode array body 54. The grasping handle 68 is made of silicone having a hardness of about 50 durometer on the Shore A scale.

Retinal tacks necessarily cause some damage to the retina. This is not of great importance since retinal arrays are only implanted in defective retinas. However, it is important not to damage the stimulated portion of the retina, or nerves and blood vessels that supply the stimulated portion of the retina. Hence, the mounting aperture 66 is placed off center and the retinal array body 54 is oriented such that the electrodes 56 fall between the tack 10 and the optic nerve (not show).

Figure 4:
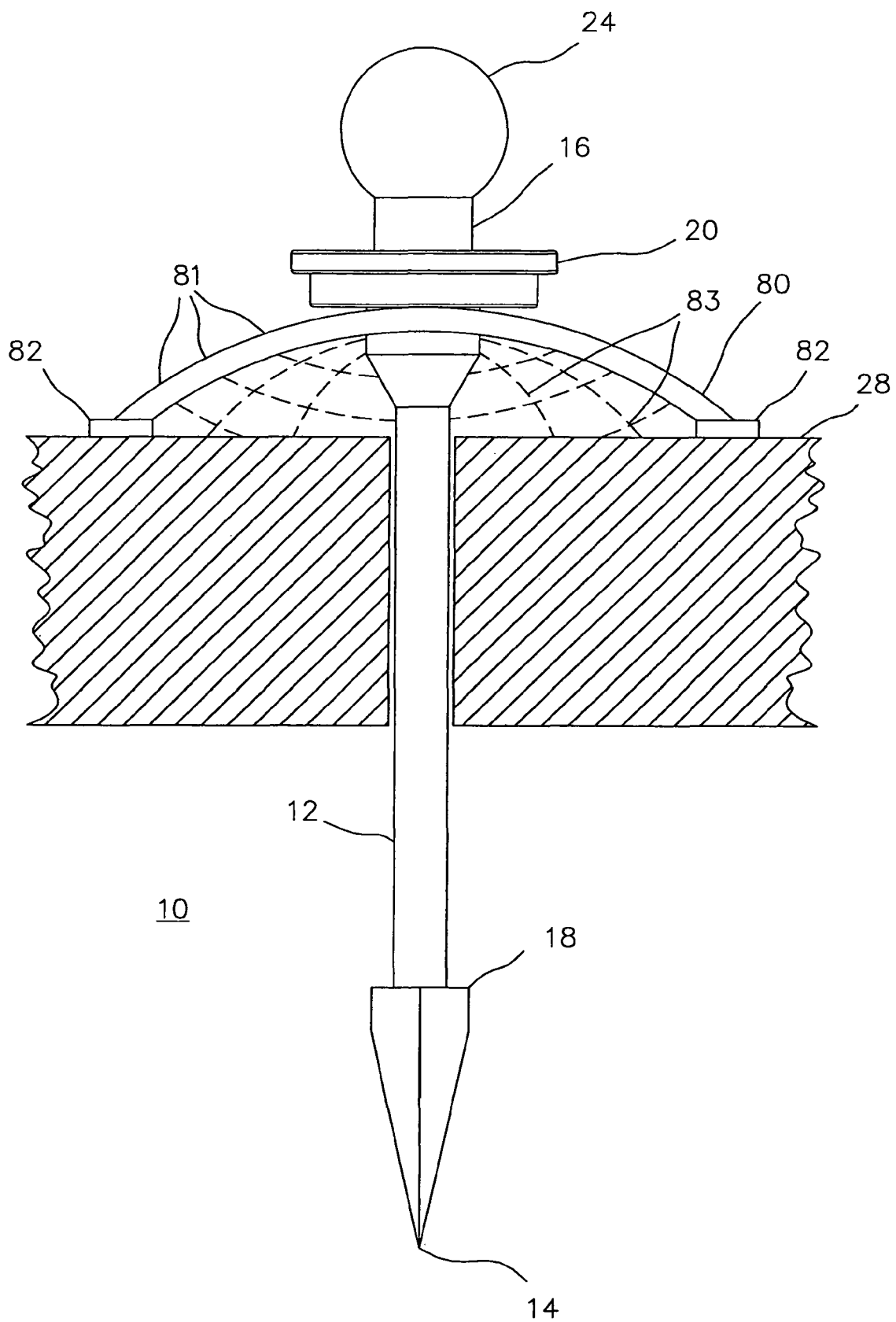
FIG. 4 is a cross section of a dome spring alternate embodiment of the retinal tack, according to the present invention.

FIG. 4 shows an alternate retinal tack 10. It should be noted that while only FIG. 2 shows the tack 10 inserted in body tissue, it should be obvious to one skilled in the art that the other tacks shown can be inserted in the same manner. The tack 10 includes the shaft 12 having point 14 and base 16. Just behind the point 14 is the barb 18. The flange 20 is formed around the base 16 of the tack 10 to form a seat for a dome spring 80 surrounding the shaft 12. The mounting stud 24 extends beyond the flange 20 to provide an access point for the insertion tool. The dome spring 80 spreads its force over a greater area than the coil spring 22. However, a washer 82 under the bottom edge of the dome spring 80 is still helpful to spread the contact area with the retinal electrode array 28.

It should be noted that a dome is normally a highly rigid structure. To achieve a resilient structure, as required here, the dome should be very thin, slotted, or made of a soft elastomer material such a silicone. Elastomer dome springs are commonly used in keyboards. A slotted dome can be made with vertical slots 81, or spiral slots 83. Spiral slots 83, or a coil spring made in the shape of a dome, can create a spring that has the advantages of coil spring 22 and dome spring 80. The dome shaped coil spring resembles those found in flashlights, except significantly smaller. A dome shaped coil spring provides the force spreading of a dome, and the softness and long range of a coil spring. A dome shaped coil spring provides a longer range than a cylindrical coil spring due to the dome shaped coil spring's ability to fold inside itself.

Figure 5:
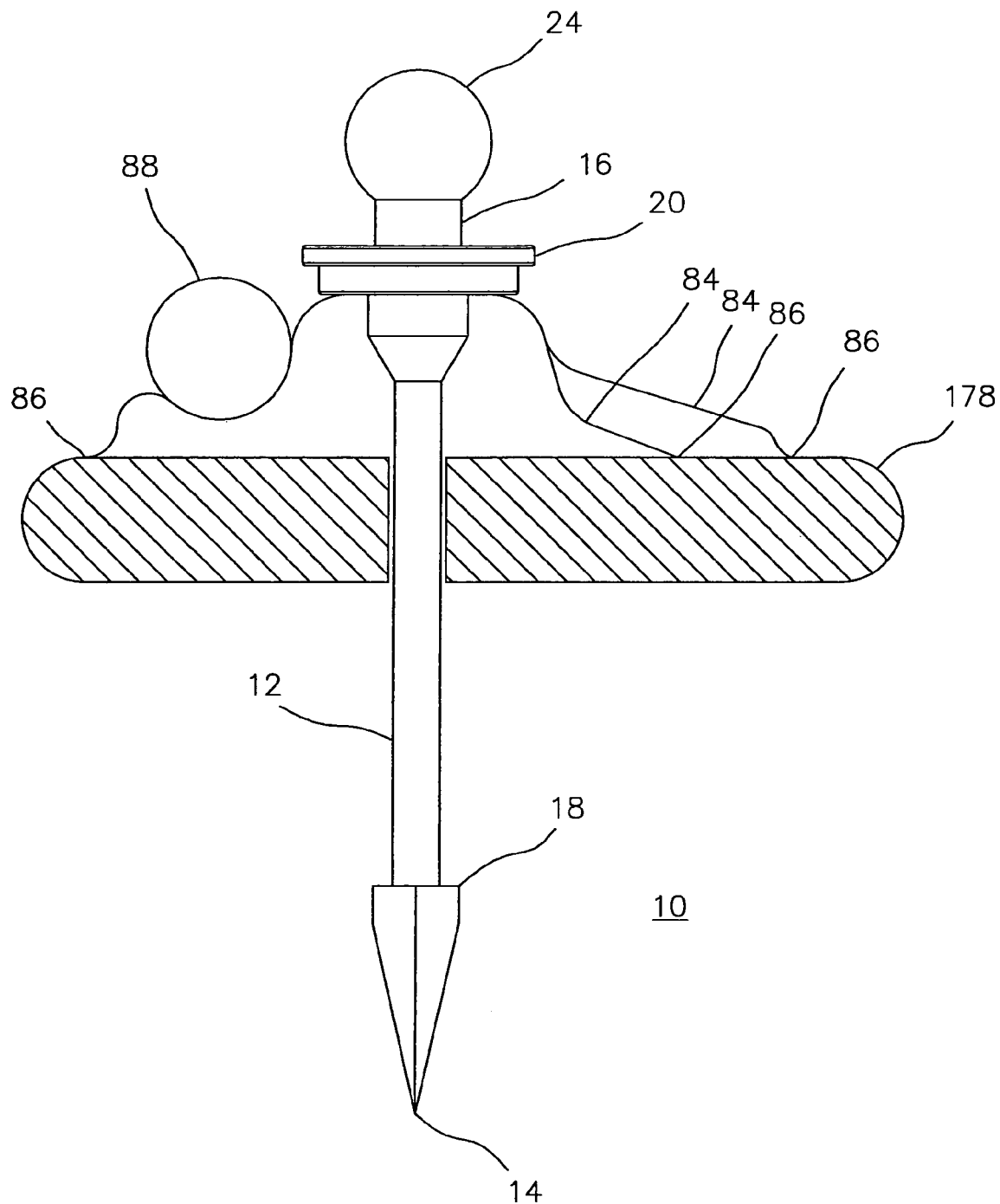
FIG. 5 is a cross section of a leaf spring alternate embodiment of the retinal tack, according to the present invention.

FIG. 5 shows an alternate retinal tack 10. The leaf springs 84, like the dome spring 80, spread their force over a greater area than the coil spring 22. However, contact pads 86 under the bottom edge of each leaf spring 84 are still helpful to provide even contact with a retinal electrode array 28. As described in FIG. 3, the mounting aperture 66 in retinal array 28 is off center. The alternate embodiment shown in FIG. 5, allows for leaf springs 84 of varying lengths to provide more even force on the retinal electrode array 28, and to protect the retinal electrode array 28 from damage. Shorter springs tend to be more rigid. To achieve even force at multiple contact points on the retinal electrode array 28, each leaf spring 84 can be manufactured in a different material, thickness or shape. Generally, longer leaf springs need to be thicker and/or straighter. Shorter leaf springs need to be thinner, and/or more curved. Leaf springs 84 may include a loop 88, to make the spring softer. Depending on the spring material used, all leaf springs 84 may require a loop 88 to achieve the correct force on the retinal electrode array 28. As described earlier, the total force should be very small, preferably limited to about 4 grams total across all of the leaf springs.

In addition to those shown here, nearly limitless spring arrangements can be designed by one skilled in the spring art. Further, materials with elastic properties, such a silicone, can be used in place of a spring. A silicone washer, such as washer 26 shown in FIG. 2, can be constructed of suitable thickness and softness to act as a spring.

Figure 6:
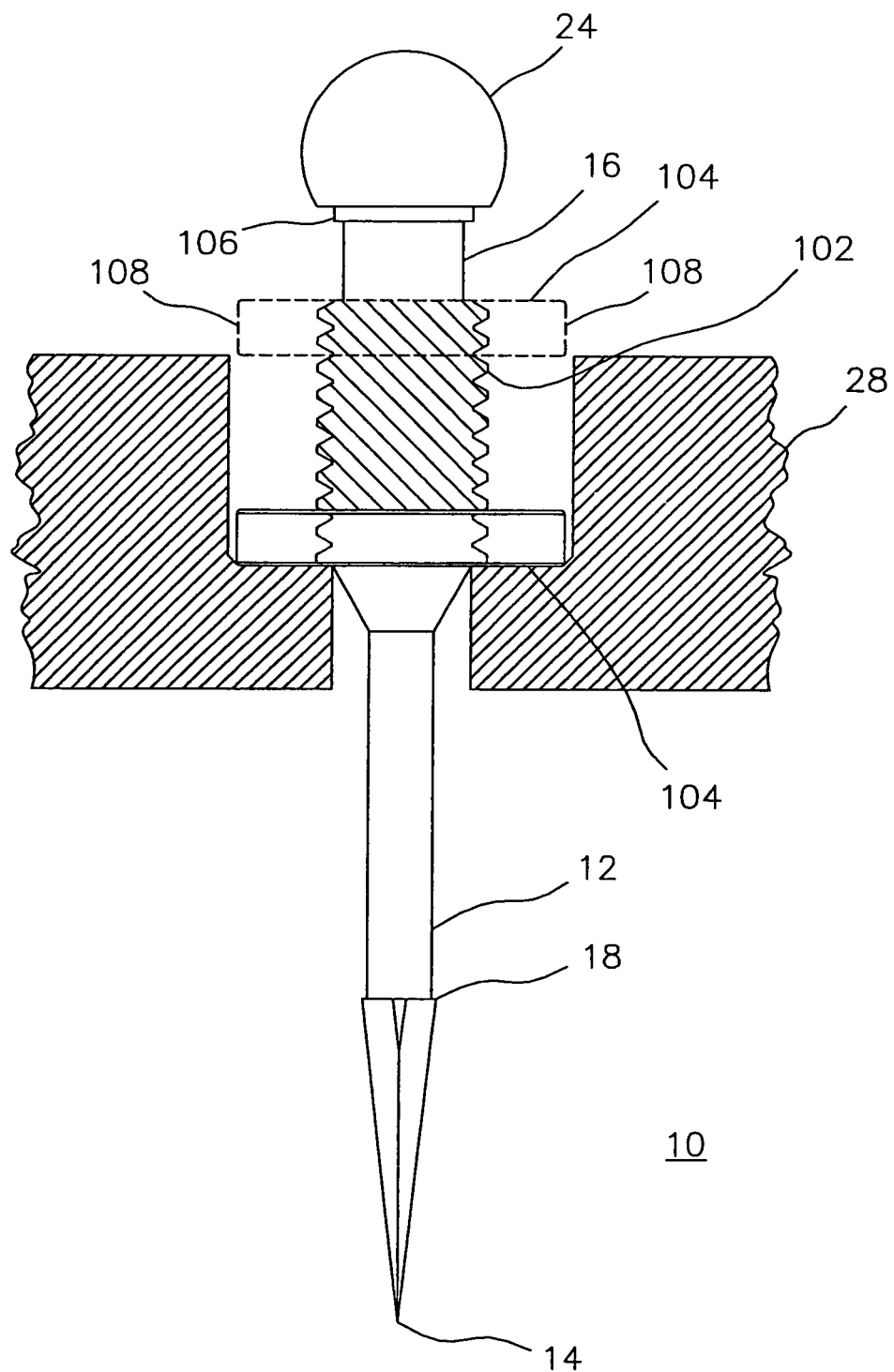
FIG. 6 is a cross section of a screw alternate embodiment of the retinal tack, according to the present invention.

FIG. 6 depicts another embodiment of the present invention. The tack 10 in this embodiment includes threads 102 and a nut 104. The nut 104 acts like the washer 20 to spread the force applied to the retinal electrode array 28. It this embodiment, the effective length of the tack 10, and thereby the force applied, is adjusted by tightening or loosening the nut 104. The tack 10 includes a bolt head 106 to prevent rotation of the tack 10, while rotating the nut 104. The nut 104 includes notches 108 to allow engagement with the insertion tool described below with reference to FIGS. 7 and 8. Implanting the retinal electrode 28 and the tack 10 into an eye, and then turning the nut 104, while not turning the tack 10, is not simple.

FIG. 7 depicts an insertion tool 120 for both inserting the tack 10 and adjusting the nut 104. The insertion tool 120 includes three long tubes nested within each other. Innermost is the tack holding tube 122 including a half circular tack receiver 124 ending in a lip 126. The tack mounting stud 24 nests within the tack receiver 124. The lip 126 at the end of the tack receiver 124 contacts the bolt head 106, and prevents the tack 10 from rotating. The tack holding tube moves through a stationary tube 128, such that when the tack receiver 124 holds a mounting stud 24 and is drawn into the stationary tube 128, the tack 10 is held firmly. However, when the tack holding tube 122 is moved forward exposing the tack receiver 126, the mounting stud 24 is free to move out of the tack receiver 126. A wrench tube 130 surrounds the stationary tube 128 and contacts the nut 104. This is shown more clearly in FIG. 8. The wrench tube 130 includes teeth 132 to engage the notches 108, and turn the nut 104. The insertion tool 120 is adapted to insert the tack described in FIG. 6. However, the insertion tool 120 is capable of inserting any of the alternate tacks described in this application. A variation of insertion tool 120 without the wrench tube 130 would be capable of inserting the tacks described in FIGS. 1, 2, 4, and 5.

Figure 9:
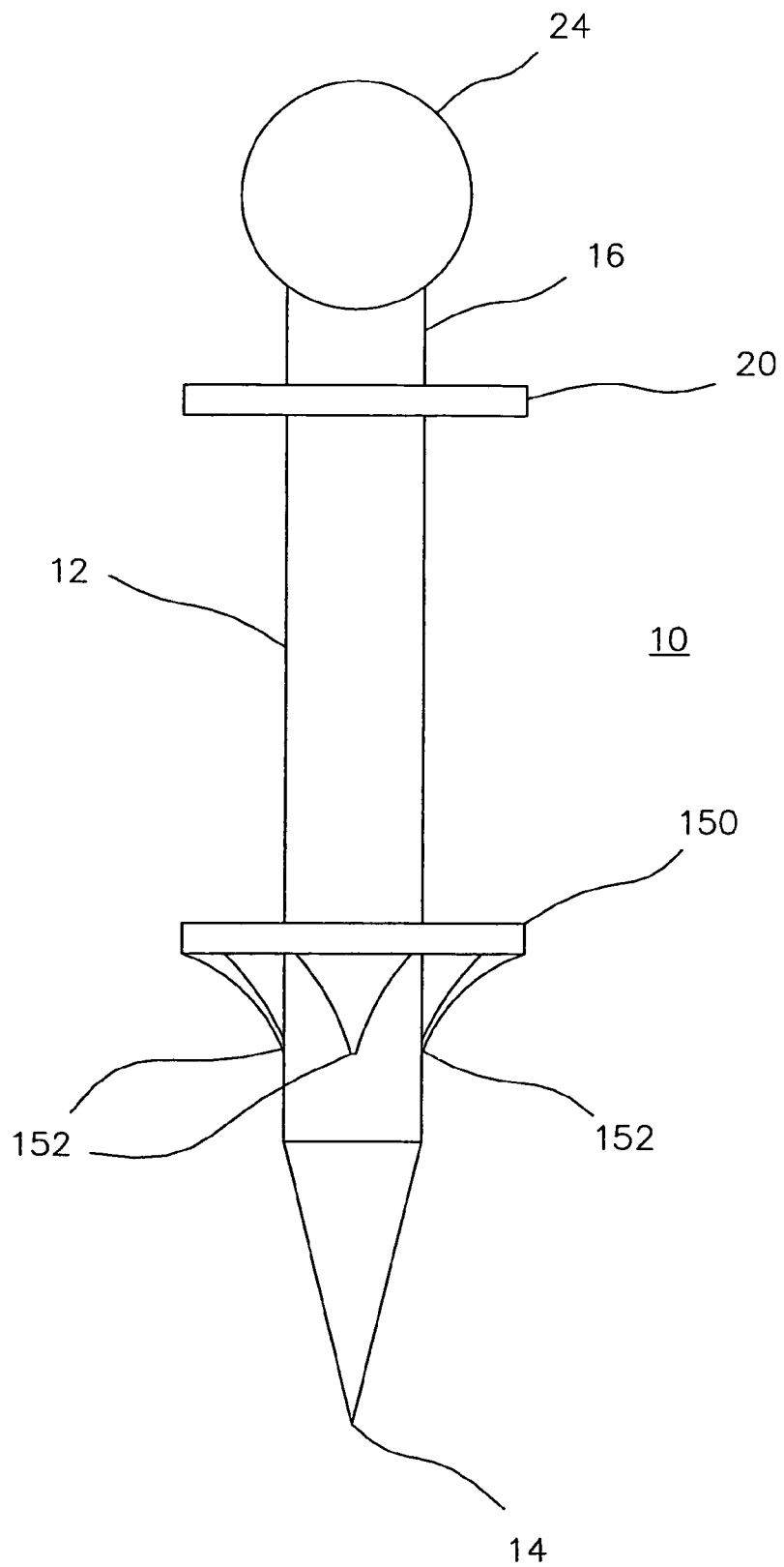
FIG. 9 is a cross section view of a tie tack alternate embodiment of the retinal tack, according to the present invention.

In the tack 10 shown in FIG. 9, the rear anchor point is the fixed flange 20, and the front anchor point varies with the thickness of the sclera. The front anchor point is a lock ring 150, including spring teeth 152. As the tack 10 pierces the lock ring 150, the spring teeth 152 are deflected. The shaft 12 can slide easily in the direction of deflection. However, any attempt to withdraw the tack 10 from the lock ring 150 will cause the spring teeth 152 to engage the shaft 12. While this embodiment does not include the barb 18, the shaft 12 may includes a series of ridges to help the spring teeth 152 engage the shaft 12. A further variation may include threads on the shaft 12 and a nut in place of lock ring 150. While the alternate embodiment achieves a high reliability of fixation of the tack 10, it requires more complicated surgery, as it requires accessing the back of the sclera.

The above detailed description is provided to illustrate the specific embodiments of the present invention and is not intended to be limiting. Numerous variations and modifications are possible within the scope of the present invention. For example, the tack of the present invention can be applied to a wide range of medical devices which require attachment to tissue of varying thickness. The tack of the present invention can also be used for tissue repair, such as to reattach a detached retina, or reattach a torn eardrum, either alone or with a patch. The present tack can also be used for gut repair by overlapping the torn gut and attaching it with the tack of the present invention. The present tack can be used for attaching other electrodes such as a spinal chord electrode or cortical electrode. A cortical electrode can be attached by piercing a gyrus with a spring tack. The present invention is defined by the following claims.

What is claimed is:

1. A medical tack for attaching a medical device to a body tissue, the medical tack comprising:
    a shaft having a pointed end and a base end, the pointed end having a point adapted to cut and pierce the body tissue and allow the medical tack to be inserted through the body tissue; a barb near the pointed end suitable to engage the tissue on a first side of the tissue;
    a movable washer near the base end suitable to be located on a side of the tissue opposite the first side;
    a means for varying an insertion length of the medical tack in the body tissue based on thickness of the body tissue which the medical tack is adapted to be inserted through, the means for varying the insertion length being located between the barb at a first location and the movable washer at a second location along the medical tack, the means for varying the insertion length being configured to vary a distance between the first location and the second location to correspondingly vary the insertion length of the medical tack, such that when the distance between the first location and the second location is shortened, the insertion length is correspondingly decreased and vice versa;
    wherein the means for varying maintains a controlled force on the body tissue;
    wherein the medical tack is of a size and material suitable to be chronically implanted within a body.

2. The medical tack according to claim 1, wherein the medical tack is a retinal tack.

3. The medical tack according to claim 2, wherein the shaft is sized such that the retinal tack is adapted to pierce a retinal device, a retina and a sclera such that the barb formed near said pointed end abuts a back side of the sclera and tends to prevent the retinal tack from being withdrawn.

4. The medical tack according to claim 1, wherein the pointed end shape adapted to pierce the body tissue is a substantially sharp conical shape.

5. The medical tack according to claim 1, wherein the base end comprises a substantially flat disc shaped surface and a mounting stud for handling the medical tack, all fixedly connected to the shaft.

6. The medical tack according to claim 5, wherein the substantially flat disc shaped surface and the mounting stud for handling the medical tack are made of a single piece of a biocompatible material.

7. The medical tack according to claim 1, wherein the means for varying the insertion length of the medical tack is a spring.

8. The medical tack according to claim 7, wherein the spring is a coil spring formed around the shaft and positioned between the first location and the second location.

9. The medical tack according to claim 7, wherein the spring is a dome spring positioned between the first location and the second location.

10. The medical tack according to claim 7, wherein the spring is a leaf spring positioned between the first location and the second location.

11. The medical tack according to claim 10, wherein the leaf spring is a plurality of leaf springs of varying lengths.

12. The medical tack according to claim 1, wherein the means for varying the insertion length exerts less than 0.2 g/mm$^2$ across surface of a retinal device.

13. A medical tack comprising:
a biocompatibie shaft having a pointed end, and a hilt end;
a barb near the pointed end suitable to engage the tissue on a first side of the tissue;
a movable washer near the hilt end suitable to be located on a side of the tissue opposite the first side; and
a biocompatible elastic member between said pointed end and said hilt end;
wherein the medical tack is of a size and material suitable to be chronically implanted within a body.

14. The medical tack according to claim 13, wherein said elastic member is a spring.

15. The medical tack according to claim 13, wherein said elastic member is made of silicone.

16. The medical tack according to claim 13, wherein said elastic member is a spring and made of silicone.

17. The medical tack according to claim 13, wherein said tack comprises titanium.

18. The medical tack according to claim 13, wherein said spring comprises titanium.

19. The medical tack according to claim 13, wherein said elastic member is free to move along said shaft.

20. The medical tack according to claim 13, wherein a first side of said elastic member is attached to said hilt end.

21. The medical tack according to claim 20, wherein a second side of said elastic member is free to move along said shaft.

* * * * *